US009726625B2

(12) United States Patent
Hill

(10) Patent No.: US 9,726,625 B2
(45) Date of Patent: Aug. 8, 2017

(54) METHOD AND SYSTEM FOR PERFORMING EDS ANALYSIS

(71) Applicant: Carl Zeiss Microscopy Ltd., Cambridge (GB)

(72) Inventor: Edward Hill, Huntingdon (GB)

(73) Assignee: Carl Zeiss Microscopy Ltd., Cambridge (GB)

( * ) Notice: Subject to any disclaimer, the term of this patent is extended or adjusted under 35 U.S.C. 154(b) by 175 days.

(21) Appl. No.: 14/824,255

(22) Filed: Aug. 12, 2015

(65) Prior Publication Data

US 2016/0061754 A1  Mar. 3, 2016

(30) Foreign Application Priority Data

Aug. 29, 2014 (EP) .................................... 14002994

(51) Int. Cl.
*G01N 23/00* (2006.01)
*G01N 23/225* (2006.01)

(52) U.S. Cl.
CPC ... *G01N 23/2252* (2013.01); *G01N 2223/402* (2013.01); *G01N 2223/616* (2013.01); *G01N 2223/66* (2013.01)

(58) Field of Classification Search
None
See application file for complete search history.

(56) References Cited

U.S. PATENT DOCUMENTS

| | | | | |
|---|---|---|---|---|
| 6,140,643 | A * | 10/2000 | Brown | G01N 23/063 378/48 |
| 6,281,024 | B1 * | 8/2001 | Yoshitake | H01L 21/67253 257/48 |
| 7,205,555 | B2 * | 4/2007 | Okuda | G06T 7/0004 250/306 |
| 2006/0028643 | A1 | 2/2006 | Gottlieb et al. | |
| 2011/0144922 | A1 * | 6/2011 | Corbett | H01J 37/28 702/28 |
| 2014/0001356 | A1 * | 1/2014 | Buhot | G21K 7/00 250/307 |
| 2014/0117229 | A1 | 5/2014 | Owen | |
| 2014/0117230 | A1 | 5/2014 | Owen et al. | |
| 2014/0117231 | A1 | 5/2014 | Owen et al. | |
| 2014/0117234 | A1 | 5/2014 | Owen | |

FOREIGN PATENT DOCUMENTS

| | | | | |
|---|---|---|---|---|
| AU | EP 1779098 A1 * | 5/2007 | ......... | G01N 23/2206 |
| EP | 1779098 A4 * | 6/2009 | ......... | G01N 23/2206 |
| EP | 1 779 098 B1 | 6/2012 | | |
| EP | 1779098 B1 * | 6/2012 | ......... | G01N 23/2206 |
| WO | WO 2014/065991 A1 | 5/2014 | | |
| WO | WO 2014/065992 A1 | 5/2014 | | |
| WO | WO 2014/065993 A1 | 5/2014 | | |
| WO | WO 2014/065994 A1 | 5/2014 | | |
| WO | WO 2014065991 A1 * | 5/2014 | ......... | G01N 23/2252 |
| WO | WO 2014065992 A1 * | 5/2014 | ............. | H01J 37/28 |
| WO | WO 2014065993 A1 * | 5/2014 | ......... | G01N 23/2252 |
| WO | WO 2014065994 A1 * | 5/2014 | ......... | G01N 23/2252 |

OTHER PUBLICATIONS

Extended European search report for corresponding EP application No. 14 002 994.3 dated Feb. 20, 2015.

* cited by examiner

*Primary Examiner* — Andrew Smyth
(74) *Attorney, Agent, or Firm* — Fish & Richardson P.C.

(57) ABSTRACT

The disclosure provides methods and systems for identifying materials using charged particle beam systems combined with x-ray spectroscopy systems.

20 Claims, 3 Drawing Sheets

METHOD AND SYSTEM FOR PERFORMING EDS ANALYSIS

CROSS-REFERENCE TO RELATED APPLICATIONS

This application claims benefit under 35 U.S.C. §119 to European Application No. 14 002 994.3, filed Aug. 29, 2014, the entire contents of which are incorporated by reference herein.

FIELD

The present invention relates to methods and systems for identifying materials using charged particle beam systems combined with x-ray spectroscopy systems.

BACKGROUND

Charged particle beam systems are conventionally used for material analysis. One method of material analysis using a charged particle beam system includes recording microscopic images of a sample by detecting secondary electrons or backscattered electrons generated by an electron beam scanned across a surface of the sample. An analysis of the recorded images provides, for example, information on the morphology of the sample. Another method of material analysis using a charged particle beam system includes detecting x-rays generated by a particle beam incident on the sample. An analysis of the detected x-rays may provide information on the elemental composition of the sample.

A material present at a given location on a sample can be identified by using a charged particle beam system to direct an electron beam onto the given location on a sample, and the x-ray spectroscopy system is used to detect a spectrum of x-rays coming from the sample in response to the electron beam directed onto the sample. The x-ray spectrum is analyzed in order to identify the material which is present at the location where the electron beam is incident on the sample. Such analysis is called "energy dispersive x-ray analysis" or "EDS". The electron beam causes electrons from inner shells of the atoms of the material to be ejected, and electrons from outer shells drop to the inner shells and emit x-rays having an energy corresponding to the energy difference between the outer and inner electron shells of the atom. These x-rays are detected by the x-ray spectroscopy system. Since each chemical element has a unique atomic structure, the chemical element can be identified by an analysis of its x-ray spectrum. In particular, an element contained in the sample can be identified by its characteristic lines in the x-ray spectrum or by characteristic energies in the x-ray spectrum.

EDS analysis can be used, for example, to analyze samples from mines to determine the presence of valuable minerals, and decisions on the viability of a mine may be influenced by the EDS analysis. A high accuracy of the identification of minerals based on the EDS analysis is desired, accordingly. The material analysis may use a library of known materials, and an x-ray spectrum obtained from a given location on a sample can be compared with data stored in the material library in order to identify the material present at the location where the x-ray spectrum is generated. This usually works quite well in practice and allows to identify the materials present at many locations of arbitrary samples. However, it may occur that an x-ray spectrum recorded for a particular location does not match with one of the materials stored in the material library. It is then not possible to assign one of the known materials to this location of the sample, resulting in a lack of information which could be useful for the complete analysis of the sample.

SUMMARY

The present invention has been made taking the above considerations into account.

Embodiments of the present invention provide strategies to process x-ray spectra which do not correspond to a known material stored in a material library. In particular, some embodiments provide strategies for processing locations of a sample where more than one material is present rather than a single material which can be identified using a material library. In such situations, the x-ray spectrum recorded from the location is a combination of x-ray spectra corresponding to a plurality of materials. Such situations may occur, for example, if the electron beam exciting the x-rays lands on a boundary between two or more materials since the excitation volume of the electron beam has a significant size.

According to some embodiments, a method of EDS analysis of a particular sample uses a first set of materials and associated material data, wherein each material data represent properties of the associated material. Such first set of materials and material data can also be referred to as a first material library. This first set of materials can be a reduced set of materials which does not contain all known materials. For example, this first set of materials does not contain materials which are known but which are not expected to be present in the particular sample. This avoids computation time spent on comparisons with materials which are not expected to be present in the sample and allows to perform the analysis of the sample within an acceptable time.

According to some further embodiments, an electron beam is directed to a plurality of locations on a sample, and energy dispersive x-ray spectra associated with the locations are recorded. The locations on the sample can be arranged, for example, in a regular rectangular array.

According to some embodiments, each location, together with the associated energy dispersive x-ray spectrum, is analyzed in order to assign a material to the location. The method may first try to assign one material of the first set of materials to the location if this is possible. For this purpose, a first similarity criterion is provided, and it is determined that the material from the first set of materials can be assigned to the location if the first similarity criterion is fulfilled. The first similarity criterion can be determined based on the energy dispersive x-ray spectrum associated with the processed location and the first set of material data.

According to some embodiments, the material data of the material of the first set include an elemental composition range associated with the material, and the processing of the location comprises determining an elemental composition associated with the processed location based on the energy dispersive x-ray spectrum associated with the processed location. The first similarity criterion is fulfilled if the determined elemental composition falls within the elemental composition range of one of the material data of the first set of materials. It is then possible to assign the material associated with this matching elemental composition range to the processed location. For example, quartz is composed of 44 weight % of Si and 56 weight % of O. Due to unavoidable measurement errors, the elemental composition range associated with the material quartz in the first set is, for example, 40 weight % to 50 weight % of Si and 50 weight % to 60 weight % of O, and the material quartz is assigned to the processed location if the amounts of Si and O of the elemental composition determined from the x-ray spectrum fall within these ranges. If, for example, the elemental composition determined from the x-ray spectrum is 30 weight % of Si and 65 weight % of O, the similarity criterion is not fulfilled for the material quartz and it is not possible to assign the material quartz to the processed location. Moreover, if this elemental composition does not fall within one of the other elemental composition ranges of the first set, the first similarity measure is not fulfilled and it is not possible to assign a material of the first set to the processed location.

According to other embodiments, the material data of the first set include sample x-ray spectra of the associated materials, and the first similarity criterion indicates a similarity between two x-ray spectra. Such similarity measure can be calculated, for example, as the sum of squared differences between the (normalized) recorded x-ray spectrum associated with the processed location and the sample x-ray spectrum associated with the material of the first set. The first similarity criterion can be fulfilled if the similarity measure exceeds a threshold.

With the above methods, it is typically possible to assign a material to a large number of locations of a sample. Still, a number of locations may remain for which it is not possible to find suitable materials from the first set of materials. According to some embodiments, the method comprises determining a first group of locations of the plurality of locations which do not have the material of the first set of materials assigned. The locations of the first group of locations can be processed as will be further illustrated below.

According to some embodiments, a location which does not have a material assigned to it, is processed by determining a second group of locations which have a material assigned and which fulfill a first proximity criterion relative to the processed location, and by assigning at least one material to the processed location based on the materials assigned to the locations of the second group of locations. According to some embodiments herein, the first proximity criterion relative to a processed location is fulfilled for a low number of locations closest to the processed location. For example, the low number can be smaller than 50, smaller than 20 or smaller than 10. The locations of the second group are located in the neighbourhood of the processed location, and one of the neighbouring materials is also assigned to the processed location.

According to some embodiments, one location from the second group of locations is selected based on a comparison of the processed location with each location of the second group of locations, and the material assigned to the selected location is also assigned to the processed location. The selected location from the second group can be the location of the second group which has a highest similarity with the processed location. According to some embodiments herein, the highest similarity is determined based on major elements present at the processed location and the locations of the second group. The major elements at a given location are those chemical elements present at the given location with significant weight percentages. The chemical element having the highest weight percentage among all elements present at the location is the major element at this location. For example, the selecting of the location from the second group may comprise determining a major element of each location of the second group based on the material data associated with the material assigned to the location, and determining an elemental composition associated with the processed location based on the energy dispersive x-ray spectrum associated with the processed location, wherein the elemental composition includes a major element. The location of the second group having the same major element as the processed location is then selected, and the material of the selected location is assigned to the processed location.

According to other exemplary embodiments, the assigning of the material of the processed location based on the materials assigned to the locations of the second group of locations comprises selecting plural locations from the second group of locations and assuming a hypothetical mixture of the plural materials and assigning at least one material of the plural materials to the processed location if a second similarity criterion determined based on the energy dispersive x-ray spectrum associated with the processed location and the material data of the materials of the plural locations is fulfilled. For example, the second similarity criterion may indicate a similarity between two x-ray spectra. Such similarity measure can be calculated from the x-ray spectrum of the processed location and the x-ray spectrum of the hypothetical mixture of the plural materials, wherein the x-ray spectrum of the hypothetical mixture is a linear combination of the x-ray spectra of the plural materials. Moreover, it is possible to determine the proportions which the plural materials have in the hypothetical mixture and to select that material having the highest proportion in the mixture for assignment to the processed location.

According to further embodiments, locations which do not have a material assigned can be processed by a comparison with a second set of materials and associated material data, wherein each material data represent properties of the associated material and wherein the second set of materials has a higher number of materials than the first set. Also the second set of materials and material data can be referred to as a material library, wherein the second set is a comprehensive library including a large number of known materials or even all known materials. It is then possible to process the locations by comparison to the reduced first set of materials and material data, resulting in assignments of a materials to a large number of locations using reasonable computation time. Only those remaining locations, for which it is not possible to assign a material based on the reduced first set of materials and material data, the extended second set of materials and material data is used, such that the higher computational effort associated with the extended set of materials and material data is spent only on a relatively low number of locations. Similar to the first similarity criterion used for assigning the material of the first set of materials to the processed location, a third similarity criterion can be used for assigning the material of the second set of materials to the processed location. The third similarity criterion can be determined based on the energy dispersive x-ray spectrum associated with the processed location and the second set of material data.

According to some embodiments, the determining of the first group of locations which do not have the material assigned comprises selecting only locations as members of the first group for which the following requirement is fulfilled: A number of locations fulfilling a second proximity criterion relative to a given location and not having a material assigned is smaller than a threshold value. Since the assigning of the material to the location of the second group is based on neighbouring materials, this avoids such processing of locations within large areas of the sample which do not have assigned materials. This is based on the understanding that it is not too wrong to assign a material from an adjacent grain to a location close to a grain boundary of that grain, while a location within a grain of unidentified material should not be assigned the material of adjacent grains.

Again, the second proximity criterion can be fulfilled for a low number of locations closest to the given location, wherein the low number can be smaller than 50, smaller than 20, or smaller than 10.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
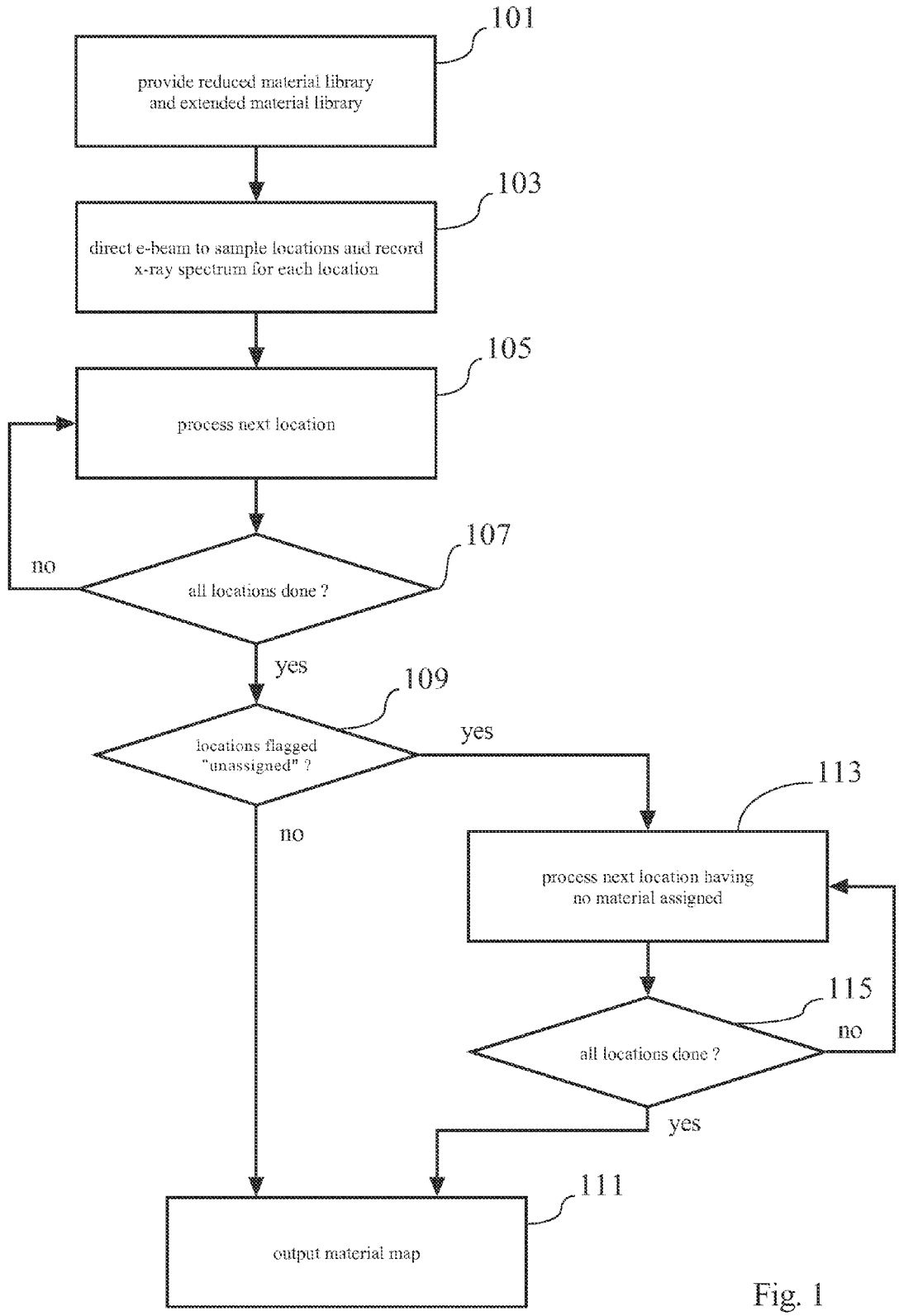
FIG. 1 shows a flow chart illustrating a method of EDS analysis.

In the exemplary embodiments described hereinafter, components that are alike in function and structure are designated as far as possible by alike reference numerals. Therefore, to understand the features of the individual components of a specific embodiment, the descriptions of other embodiments and of the summary of the disclosure should be considered.

FIG. 1 is a flow chart illustrating a method of EDS analysis of a sample. The sample can be a mineral sample, for example. The sample can be prepared such that it can be inspected using an electron microscope. The sample preparation may include cutting a section of the sample and polishing of its surface. The sample preparation may also include milling of the sample and embedding the resulting particles in a block of resin, which is also cut and polished.

The analysis is performed using a charged particle system, such as an electron microscope. The analysis may include recording of images of the sample by detecting secondary electrons and/or backscattered electrons generated by a primary electron beam scanned across the sample surface by the electron microscope. The electron microscope also includes an x-ray spectroscopy system allowing to detect x-rays excited by the incident primary electron beam.

It is assumed that a particular sample is analyzed and that some information on this sample is already available, such that some materials of all known materials are expected to be present in the sample while other known materials should not be present in the sample. A first set of materials expected to be present in the sample is provided as a reduced material library in a step 101. The illustrated method tries to assign a material from the reduced material library to an analyzed location of the sample. Only if this is not possible, the method tries to assign a material from an extended material library to the location. This extended material library is also provided in step 101. The set of materials and material data of the reduced material library can be a subset of the materials and material data of the extended material library.

The reduced and the extended material libraries contain, for each material, corresponding material data. The material data may include elemental composition ranges for elements contained in the material and/or sample x-ray spectra for the material.

In a step 103, an electron beam is directed to a plurality of locations on the sample, and an x-ray spectrum is recorded for each location. The locations and associated x-ray spectra are subsequently analyzed in a loop, wherein a next location is processed in a step 105 in which a material is assigned to the location, and a decision is made in a step 107 as to whether all locations have been processed.

Figure 2:
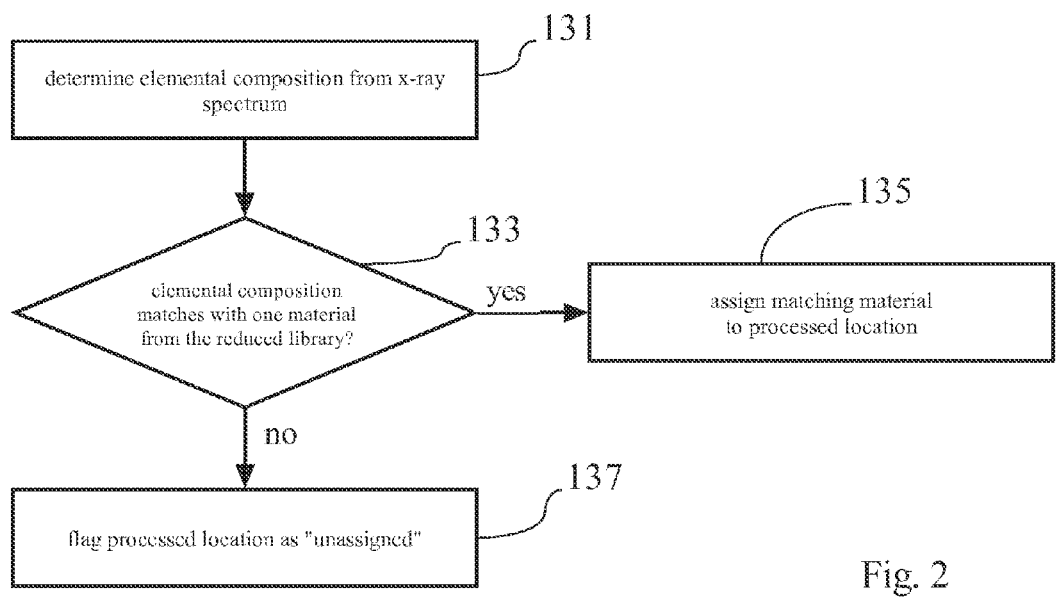
FIG. 2 shows a flow chart of a method detail of the EDS analysis shown in FIG. 1.

Details of the processing performed in step 105 are shown in the flowchart of FIG. 2.

The processing shown in FIG. 2 requires a recorded x-ray spectrum associated with the analyzed location. In a step 131, an elemental composition is determined based on the x-ray spectrum. In a step 133, the determined elemental composition is compared to elemental composition ranges of the materials contained in the reduced material library. If a matching material is found in the material library, this matching material is assigned to the processed location in a step 135, and the processing of step 105 in FIG. 1 is terminated. The determination whether one material of the reduced material library matches can be based on a similarity measure calculated based on the energy dispersive x-ray spectrum and the material data of the materials contained in the material library. The calculated similarity measure can be compared with a similarity threshold, and a material matches if the similarity measure exceeds the similarity threshold. In particular, the elemental composition determined based on the x-ray spectrum in step 131 can be compared to elemental composition ranges associated with the materials contained in the material library.

If a matching material from the material library is not found in step 133, the location is flagged as "unassigned" in a step 137, indicating that it was not possible in step 133 to assign a material of the reduced material library to the location. This can be achieved, for example, by setting an element of a data record representing the location to a predetermined value or by adding the location to a list of locations collecting all those processed locations to which it was not possible in step 113 to assign a material. This terminates the processing of step 105 in FIG. 1.

If it is determined in step 107 that all locations have been processed, the method continues with a step 109. Otherwise, the method proceeds with step 105 by analyzing a next location.

In step 109 it is determined whether one or more of the locations are flagged as "unassigned", i.e. whether it was not possible to assign a material from the reduced material library to the location in step 105. If there are no locations without an assigned material, the method terminates with a step 111. The step 111 may include outputting of a material map which indicates the correspondence between locations and materials assigned to the locations of the sample.

If it is determined in step 109 that there exist locations without an assigned material, the method performs a loop with steps 113 and 115 in order to process the unassigned locations. Each respective next location is processed in step 113 in which it is again tried to assign a material to the processed location by using strategies different from that used in step 105. Details of the processing in step 113 will be illustrated in more detail with reference to FIG. 3 below. In step 115 it is determined whether all unassigned locations have been processed. If this is true, the processing terminates with step 111. Otherwise, the next unassigned location is processed in step 113.

Figure 3:
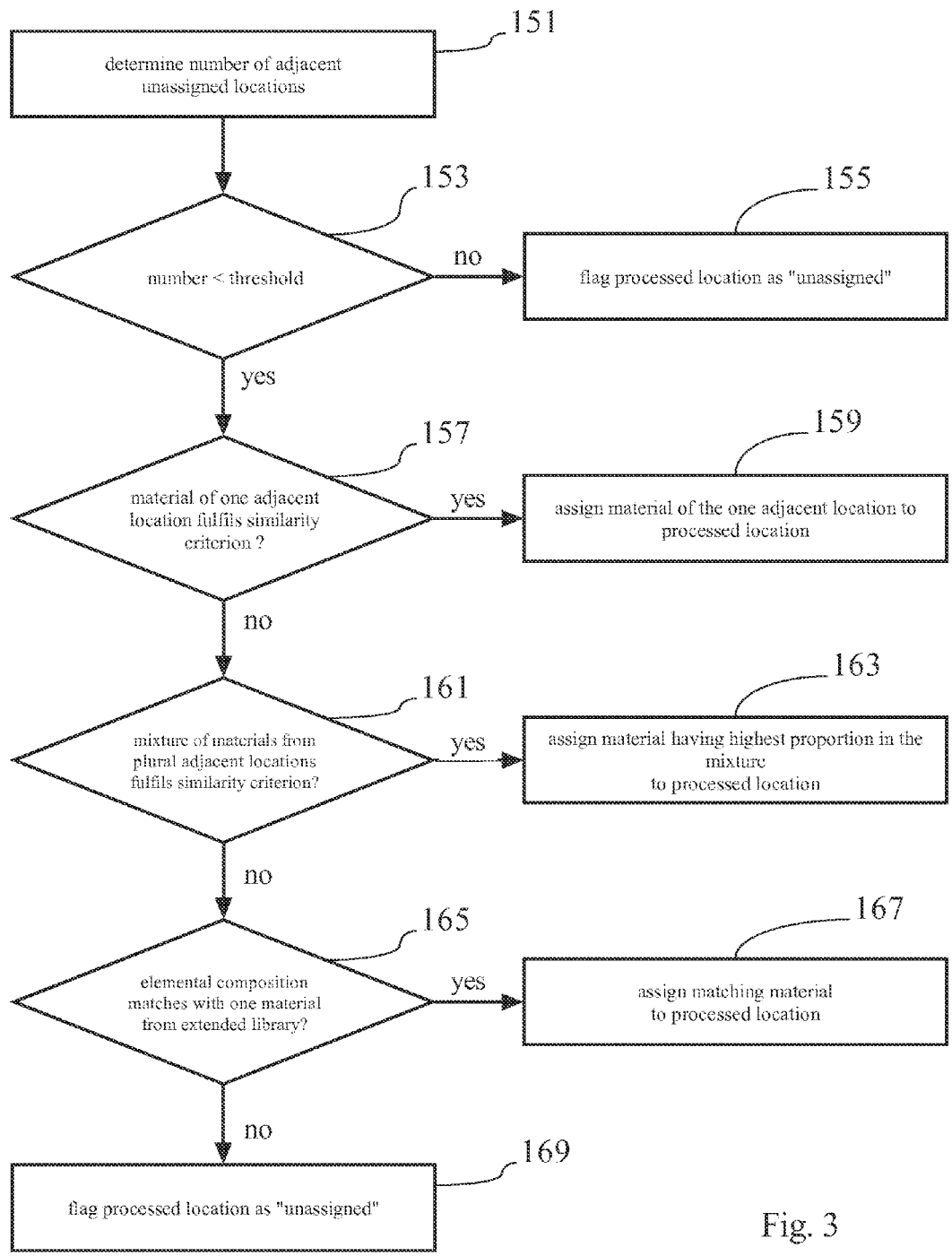
FIG. 3 shows a flow chart of a further method detail of the EDS analysis shown in FIG. 1.

Details of the processing performed in step 113 are shown in the flowchart of FIG. 3.

The processing in step 113 includes assigning of a material to the unassigned processed location based on materials already assigned to locations adjacent to this processed location. This is based on the assumption that the material at a given location is possibly similar to materials present in neighbouring locations. However, this assumption is probably not correct in a situation where the unassigned location is, for example, in the centre of a grain of an unidentified material. Therefore, a number of unassigned locations adjacent to the processed location is determined in a step 151. If this number is greater than a predetermined threshold it is decided in a step 153 that it is not possible to assign a material to the location, and it is again flagged as "unassigned" in a step 155.

If the number is smaller than the threshold, the processing continues with a step 157 in which a group of locations is determined which are adjacent to the processed location and which have an assigned material. In step 157 it is further determined whether one of the locations of this group of locations fulfills a similarity criterion with the processed location. If this is the case, the material assigned to the location fulfilling the similarity criterion is also assigned to the processed location in a step 159. For example, the similarity criterion is fulfilled if the material of the adjacent location has a same major element as the processed location.

If a location of the group of locations fulfilling the similarity criterion in step 157 is not found, the processing continues with a step 161. In step 161 it is assumed that the material at the processed location is a hypothetical mixture of materials of the materials at two or more adjacent locations, and at least one material of the adjacent locations is assigned to the processed location.

Figure 4:
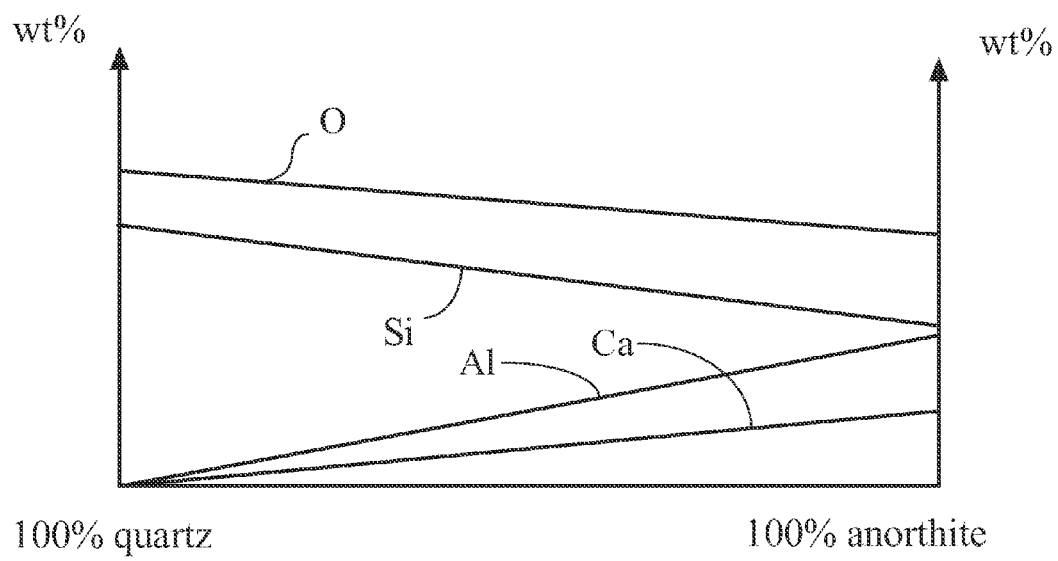
FIG. 4 shows a graph illustrating a detail of FIG. 3.

An example of such processing will now be illustrated with reference to FIG. 4. It is assumed that a first adjacent location has the assigned material quartz and a second adjacent location has the assigned material anorthite. Quartz has a composition of 47 weight % Si and 53 weight % O, while anorthite has a composition of 14 weight % Ca, 20 weight % Al, 20 weight % Si and 46 weight % O. It is further assumed that the elemental composition determined from the X-ray spectrum at the processed location amounts to 26.75 weight % Si, 10.5 weight % Ca, 15 weight % Al and 47.75 weight % O. It is assumed that the material at the processed location is a hypothetical mixture of quartz and anorthite. FIG. 4 shows the elemental composition of such mixture depending on the quartz and anorthite proportions in the mixture. It is apparent that Ca and Al are only present in one of the materials, namely anorthite. Based on the amount of Ca contained in the hypothetical mixture based on the elemental composition determined from the x-ray spectrum, it can be determined that the hypothetical mixture contains 75% anorthite and 25% quartz. In an exemplary method, the material having the highest proportion in the mixture, i.e. anorthite, is assigned to the processed location in a step 163.

If it is not possible to assign a material from the adjacent locations to the processed location using a suitable similarity measures in step 161, the procedure continues at a step 165. In step 165 the elemental composition of the processed location determined in step 131 is compared to the extended material library. This material library contains a higher number of materials than the material library used in step 133 and may, in particular, contain all known materials. If a matching material is found in step 165 based on a suitable similarity measure, this matching material is assigned to the processed location in a step 167.

If it is not possible to find a matching material in step 165, the processing continues at a step 169. In step 169, the location is again flagged as a location without an assigned material.

The above method can be performed automatically, i.e. the material map outputted in step 111 is generated without manual intervention by an operator. This does not prevent, however, an operator from processing the locations flagged as "unassigned" manually.

After the above described method is performed, a statistical analysis based on the assigned material data can be conducted. For example, a medium grain size of particles of a particular mineral can be calculated based on dimensions of neighbouring locations to which this particular mineral is assigned. As an alternative example, the average content of one or more particular minerals can be calculated based on a ratio of the number of locations to which this particular mineral is assigned relative to an overall number of locations or relative to a number of locations to which another mineral is assigned. After statistical analysis based on the assigned material data are performed, results of such statistical analysis are presented on an output device to an operator. The output device can be a display device. Alternatively the output device can be a printer with which reports of the results are generated in a desired format.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the scope of the present disclosure as defined in the following claims.

The invention claimed is:

1. A method, comprising:
providing a first set of materials and associated material data, each material data representing properties of an associated material of the first set of materials;
directing an electron beam to a plurality of locations on a sample and recording an energy dispersive x-ray spectrum associated for each location of the plurality of locations;
processing each location of the plurality of locations by:
assigning a material of the first set of materials to a processed location when a first similarity criterion determined based on the energy dispersive x-ray spectrum associated with the processed location and the first set of material data is fulfilled; and
determining a first group of locations which do not have the material of the first set of materials assigned; and
processing locations of the first group of locations by:
determining a second group of locations which have the material of the first set of materials assigned and which fulfil a first proximity criterion relative to the processed location; and
assigning at least one material of the first set of materials to the processed location based on the materials assigned to the locations of the second group of locations.

2. The method of claim 1, wherein assigning the at least one material to the processed location based on the materials assigned to the locations of the second group of locations comprises selecting one location from the second group of locations based on a comparison of the processed location with each location of the second group of locations, wherein the material assigned to the selected location is assigned to the processed location.

3. The method of claim 2, wherein selecting the location from the second group of locations comprises selecting a location from the second group of locations which has a highest similarity with the processed location.

4. The method of claim 3, wherein selecting the location from the second group of locations comprises:
determining a major element for each location of the second group of locations based on the material data associated with the material assigned to the location;
determining an elemental composition associated with the processed location based on the energy dispersive x-ray spectrum associated with the processed location, the elemental composition comprising a major element; and
selecting the location comprising the same major element as the processed location.

5. The method of claim 2, wherein selecting the location from the second group of locations comprises:
determining a major element for each location of the second group of locations based on the material data associated with the material assigned to the location;
determining an elemental composition associated with the processed location based on the energy dispersive x-ray spectrum associated with the processed location, the elemental composition comprising a major element; and
selecting the location comprising the same major element as the processed location.

6. The method of claim 1, wherein assigning the material to the processed location based on the materials assigned to the locations of the second group of locations comprises:
selecting plural locations from the second group of locations; and
assuming a hypothetical mixture of plural materials and assigning at least one material of the plural materials to the processed location when a second similarity criterion determined based on the energy dispersive x-ray spectrum associated with the processed location and the material data of the materials of the plural locations is fulfilled.

7. The method of claim 6, further comprising selecting a material of the hypothetical mixture having a highest proportion from the plural materials and assigning the selected material to the processed location.

8. The method of claim 7, further comprising providing a second set of materials and associated second material data, wherein:
the second set of materials has a larger number of materials than the first set of materials;
each second material data represent properties of an associated material of the second set of materials; and
when the second similarity criterion is not fulfilled, assigning a material of the second set of materials to the processed location when a third similarity criterion determined based on the energy dispersive x-ray spectrum associated with the processed location and the second set of material data is fulfilled.

9. The method of claim 6, further comprising providing a second set of materials and associated second material data, wherein:
the second set of materials has a larger number of materials than the first set of materials;
each second material data represent properties of an associated material of the second set of materials; and
when the second similarity criterion is not fulfilled, assigning a material of the second set of materials to the processed location when a third similarity criterion determined based on the energy dispersive x-ray spectrum associated with the processed location and the second set of material data is fulfilled.

10. The method of claim 1, wherein:
the material data of the material of the first set comprise an elemental composition range associated with the material;
the processing of each location of the plurality of locations comprises determining an elemental composition associated with the processed location based on the energy dispersive x-ray spectrum associated with the processed location; and
the first similarity criterion is fulfilled for a material of the first set when the elemental composition associated with the processed location falls within the elemental composition range of this material.

11. The method of claim 1, wherein:
the material data of the material of the first set comprise sample x-ray spectra of the materials; and
the first similarity criterion is fulfilled for a material of the first set when a first similarity measure between the energy dispersive x-ray spectrum associated with the processed location and the sample x-ray spectrum of this material exceeds a first similarity threshold.

12. The method of claim 1, wherein the first proximity criterion relative to the processed location is fulfilled for fewer than 50 locations closest to the processed location.

13. The method of claim 1, wherein the first proximity criterion relative to the processed location is fulfilled for fewer than 20 locations closest to the processed location.

14. The method of claim 1, wherein the first proximity criterion relative to the processed location is fulfilled for fewer than 10 locations closest to the processed location.

15. The method of claim 1, wherein determining the first group of locations which do not have the material assigned comprises selecting only locations as members of the first group for which a number of locations fulfilling a second proximity criterion relative to a given location and not having a material assigned is smaller than a threshold value.

16. The method of claim 15, wherein the second proximity criterion relative to the given location is fulfilled for fewer than 50 locations closest to the given location.

17. A computer program product residing on a computer readable hardware storage device, the computer program product comprising instructions for causing a system to perform the method of claim 1.

18. A method, comprising:
recording an energy dispersive x-ray spectrum associated for each location of a plurality of locations of a sample;
processing each location of the plurality of locations by:
assigning a material of a first set of materials to a processed location when a first similarity criterion determined based on the energy dispersive x-ray spectrum associated with the processed location and a first set of material data associated with the material is fulfilled; and
determining a first group of locations which do not have the material of the first set of materials assigned; and
processing locations of the first group of locations by:
determining a second group of locations which have the material of the first set of materials assigned and which fulfil a first proximity criterion relative to the processed location; and assigning at least one material of the first set of materials to the processed location based on the materials assigned to the locations of the second group of locations.

19. The method of claim 18, further comprising directing a charged particle beam to the plurality of locations of the sample to generate the energy dispersive x-ray spectrum associated with each location of the plurality of locations.

20. The method of claim 19, wherein the charged particle beam comprises an electron beam.

* * * * *